United States Patent
Magnusson et al.

(10) Patent No.: US 10,821,026 B2
(45) Date of Patent: Nov. 3, 2020

(54) WELDING PROTECTOR WITH MAGNIFYING COVER

(71) Applicant: 3M INNOVATIVE PROPERTIES COMPANY, St. Paul, MN (US)

(72) Inventors: Kristina M. Magnusson, Djurmo (SE); Britton G. Billinglsey, St. Paul, MN (US); Christopher M. Brown, Cottage Grove, MN (US); Timothy L. Wong, St. Paul, MN (US); Kenneth Jarefors, Borlänge (SE); John M. Kruse, Minneapolis, MN (US); Jon A. Kirschhoffer, Stillwater, MN (US); John M. Pilgrim, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 64 days.

(21) Appl. No.: 16/096,338

(22) PCT Filed: Apr. 24, 2017

(86) PCT No.: PCT/US2017/029055
§ 371 (c)(1),
(2) Date: Oct. 25, 2018

(87) PCT Pub. No.: WO2017/189394
PCT Pub. Date: Nov. 2, 2017

(65) Prior Publication Data
US 2019/0125586 A1  May 2, 2019

(30) Foreign Application Priority Data
Apr. 27, 2016 (EP) ..................................... 16167182

(51) Int. Cl.
*A61F 9/06* (2006.01)
*B23K 9/32* (2006.01)
(Continued)

(52) U.S. Cl.
CPC .............. *A61F 9/067* (2013.01); *B23K 9/322* (2013.01); *F16P 1/06* (2013.01); *G02C 7/101* (2013.01);
(Continued)

(58) Field of Classification Search
CPC .. A61F 9/067; A61F 9/06; A61F 9/064; A61F 9/061; A61F 2250/0053;
(Continued)

(56) References Cited

U.S. PATENT DOCUMENTS 701,788 A     6/1902  Berger
1,530,240 A *  3/1925  Crawford ................. G02C 7/02
                                                351/60
(Continued)

FOREIGN PATENT DOCUMENTS

CN   105213093 A   1/2016
CN   105455947 A   4/2016
(Continued)

OTHER PUBLICATIONS

International Search Report for PCT International Application No. PCT/US2017/029055, dated Aug. 4, 2018, 6 pages.
(Continued)

*Primary Examiner* — Robert H Muromoto, Jr.
(74) *Attorney, Agent, or Firm* — Gregg H. Rosenblatt

(57) ABSTRACT

A welding protector (1) has a curved eye protection shield (10) with an electrically switchable light filter. The welding protector further has a magnifying cover (20) for arrangement on an eye facing inner side of the eye protection shield. The magnifying cover is pre-shaped based on a curve that extends equidistant to the curve the eye protection shield is based on. Further, the magnifying cover has two optical lenses (27) which in combination only partially cover the eye protection shield.

13 Claims, 4 Drawing Sheets

(51) Int. Cl.
*F16P 1/06* (2006.01)
*G02C 7/10* (2006.01)
*G02F 1/1335* (2006.01)
*G02F 1/1337* (2006.01)
*A61F 9/02* (2006.01)

(52) U.S. Cl.
CPC .. G02F 1/133528 (2013.01); G02F 1/133711 (2013.01)

(58) Field of Classification Search
CPC ............ A61F 2250/0062; A61F 2/1618; A61F 9/023; A61F 9/025; A61F 9/065; G02F 1/133528; G02F 1/13471; G02F 2001/1398; G02F 2001/133531; G02F 1/1396; G02F 1/1333; G02F 1/13318; A41D 13/1184
See application file for complete search history.

(56) References Cited

U.S. PATENT DOCUMENTS

| | | | | |
|---|---|---|---|---|
| 1,636,450 | A * | 7/1927 | Ames, Jr. | G02B 30/40 359/478 |
| 2,628,530 | A * | 2/1953 | Rabben | A61F 9/06 351/44 |
| 2,812,688 | A * | 11/1957 | Shiffman | G02B 25/004 359/481 |
| 3,415,595 | A * | 12/1968 | Nelson | A61F 9/06 351/44 |
| 4,240,709 | A * | 12/1980 | Hornell | A61F 9/067 349/104 |
| 4,523,808 | A * | 6/1985 | Miller | A61F 9/064 359/350 |
| 4,867,550 | A * | 9/1989 | Jannard | A61F 9/025 351/47 |
| 4,892,384 | A * | 1/1990 | Okamoto | G02B 25/004 351/159.58 |
| 5,548,448 | A * | 8/1996 | Wagner | G02B 25/005 359/802 |
| 5,966,239 | A * | 10/1999 | Shirayanagi | G02B 7/002 359/409 |
| 6,185,739 | B1 * | 2/2001 | Verkic | A61F 9/06 2/8.1 |
| 7,477,330 | B2 * | 1/2009 | Magnusson | G02F 1/13471 349/14 |
| 7,884,888 | B2 * | 2/2011 | Magnusson | G02F 1/133528 349/14 |
| 8,767,133 | B2 * | 7/2014 | Sahouani | A61F 9/067 349/122 |
| 9,038,198 | B2 * | 5/2015 | Feinberg | G02B 7/006 2/8.2 |
| 10,426,667 | B2 * | 10/2019 | Magnusson | H04N 5/2353 |
| 2003/0137635 | A1 * | 7/2003 | Suzaki | G02C 7/028 351/159.05 |
| 2005/0036105 | A1 * | 2/2005 | Perel | G02C 7/042 351/159.41 |
| 2006/0058874 | A1 * | 3/2006 | Peli | A61F 2/1618 351/159.05 |
| 2006/0203148 | A1 * | 9/2006 | Magnusson | G02F 1/133528 349/96 |
| 2007/0089215 | A1 * | 4/2007 | Biche | A61F 9/067 2/8.2 |
| 2009/0079886 | A1 * | 3/2009 | Magnusson | G02F 1/13471 349/14 |
| 2011/0299025 | A1 * | 12/2011 | Sahouani | A61F 9/067 349/194 |
| 2014/0007312 | A1 * | 1/2014 | Wright | A61F 9/064 2/8.2 |
| 2014/0013479 | A1 * | 1/2014 | Magnusson | A61F 9/067 2/8.7 |
| 2014/0168546 | A1 * | 6/2014 | Magnusson | G02F 1/133528 349/14 |
| 2017/0367891 | A1 * | 12/2017 | Magnusson | B23K 9/095 |

FOREIGN PATENT DOCUMENTS

| | | |
|---|---|---|
| EP | 0706674 | 4/1996 |
| GB | 2225646 | 6/1990 |
| WO | WO 2014-092989 | 6/2014 |

OTHER PUBLICATIONS

Search Report for CN Appl. No. 201780026180.2, dated Mar. 18, 2020, 2 pages.

* cited by examiner

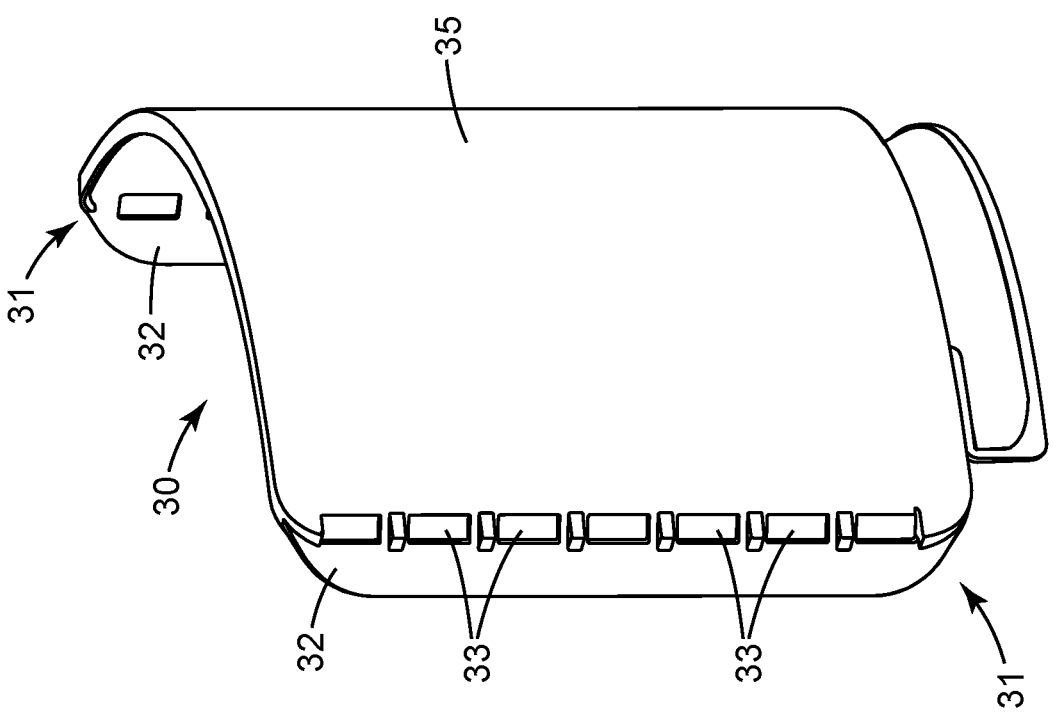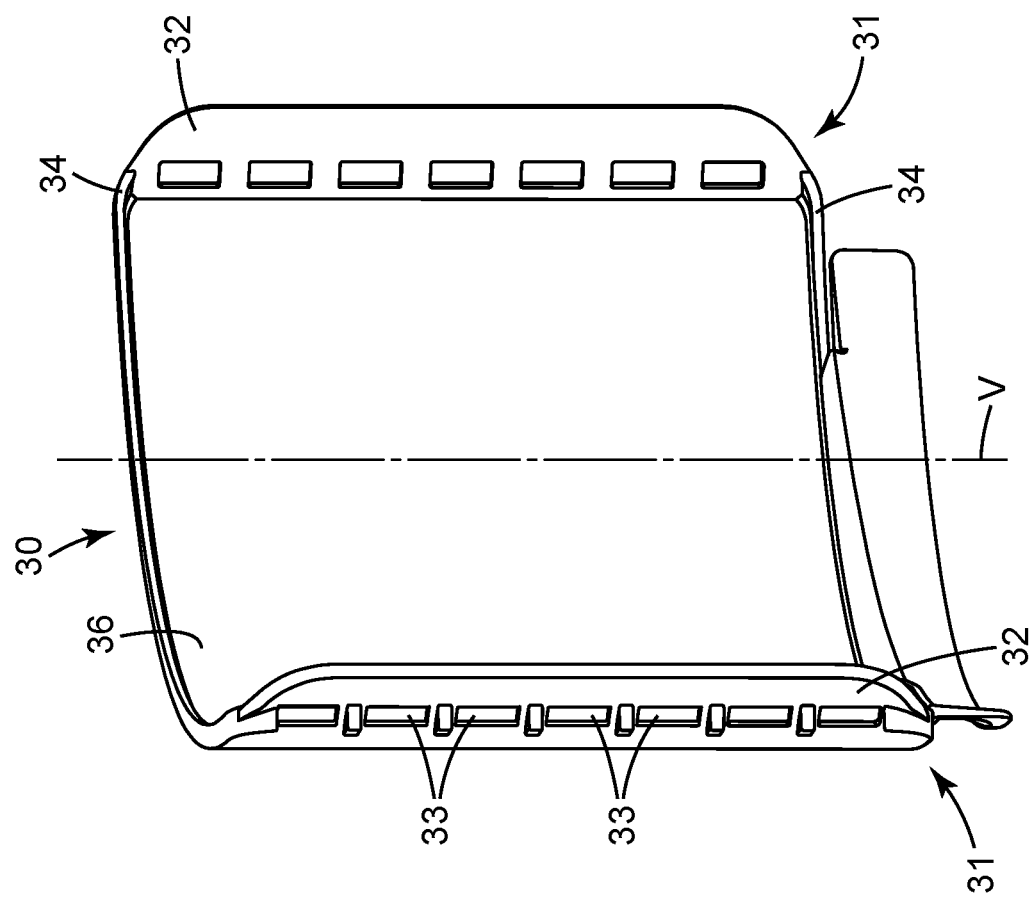
Fig. 2

WELDING PROTECTOR WITH MAGNIFYING COVER

CROSS REFERENCE TO RELATED APPLICATIONS

This application is a national stage filing under 35 U.S.C. 371 of PCT/US2017/029055, filed Apr. 24, 2017, which claims the benefit of European Application No. 16167182.1 filed Apr. 27, 2016, the disclosure of which is incorporated by reference in its/their entirety herein.

FIELD OF THE INVENTION

The invention relates to a welding protector, and in particular to a welding protector having a curved eye protection shield with an electrically switchable light filter and a magnifying cover for arrangement on the eye protection shield.

BACKGROUND ART

Automatic darkening filters commonly have a switchable filter that automatically changes from a light-transmission-state to a dark-transmission-state in response to incident light. The switching is generally achieved through use of a photodetector that is located on, or as part of, personal protective equipment. The photodetector recognizes the presence of the incident light-to-be-filtered, and an electronic module generates a control voltage that, when applied to the switchable filter, causes the filter to change from the light-transmission-state to the dark-state.

Automatic light filters have been designed which contain liquid-crystal cells located between polarizing films. U.S. Pat. No. 4,240,709 to Hornell describes a switchable filter that has a single-twisted, nematic, liquid-crystal cell sandwiched between a pair of mutually crossed polarizers. The liquid-crystal cells are optically-transparent glass substrates that include transparent electrode and alignment layers. The liquid-crystal molecules orientate themselves in a particular direction when a voltage is applied across the liquid-crystal cell under the control of an electronic module. Many commercially available products use this kind of switchable filter.

The use of an automatic-darkening filter in a protective shield gives significant ergonomic benefits. Previously welders, for example, had to "nod" their welding shield down when they struck the welding arc to ensure that their eyes were protected from the torch light. Automatic welding filters eliminate this action since the welding shield can be left in position continuously.

SUMMARY OF THE INVENTION

The invention relates to a welding protector. The welding protector may be a welding helmet covering major portions of a wearer's head or a welding shield covering viewer portions of a wearer's head. The welding protector comprises an eye protection shield that has an electrically switchable light filter. The eye protection shield has a curved shape about a vertical axis. Further, the welding protector has a magnifying cover for direct or indirect arrangement on an eye facing inner side of the eye protection shield. The magnifying cover is pre-shaped based on a curve that extends equidistant to the curve the eye protection shield is based on. Furthermore, the magnifying cover comprises two optical lenses which in combination only partially cover the eye protection shield.

For the purpose of the present specification the welding protector including its components may be defined in a three-dimensional Cartesian coordinate system, the dimensions of which may be designated based on an orientation in which the welding protector is preferably worn by a wearer. In such a coordinate system the vertical axis corresponds to a vertical dimension along the force of gravity. Further, such coordinate system defines perpendicular to the vertical dimension two horizontal dimensions which are perpendicular relative to each other and which virtually define a horizontal plane. The skilled person will recognize that although the welding protector can be worn at different orientations the vertical axis refers to an orientation in which the wearer is in an upright position.

For the purpose of the present specification the term "equidistant" refers to two curves or lines which extend at the same distance relative to each other along their length. For example two parallel straight lines are equidistant in the sense of this definition.

The curve of the eye protection shield is defined in the horizontal plane of the coordinate system. The eye protection shield extends based on this curve in the vertical dimension. For example, the curve may correspond to a neutral axis of a profile of the eye protection shield and the eye protection shield may extend with this profile in the vertical dimension.

The eye protection shield further has a height in the vertical dimension, as well as a width and a deflection in the two horizontal dimension, respectively. The width is defined in the dimension of the distance between the ends of the curve and the deflection is defined in the dimension between an imaginary line through the ends of the curve and the apex of the curve.

The invention is advantageous in that it allows a wearer to selectively use the welding protector with and without the magnifying cover. Further, the invention is advantageous in that a wearer can use the welding protector with or without viewing through the magnifying cover. Accordingly, the welding protector may be used by persons who do not need magnification under normal conditions but eventually for close-up work or work on tiny objects only. Further, the invention is advantageous in that it provides a wide viewing angle with and without viewing through the magnifying cover.

In one embodiment the optical lenses have a rectangular outline and are arranged directly adjacent each other. Further, the optical lenses may extend over the entire or substantially the entire width of the eye protection shield. This maximizes the viewing angle at which objects may be viewed magnified by a wearer.

In a further embodiment the welding protector has an inner protection cover. The inner protection cover is preferably removably attachable in a position adjacent the inner side of the eye protection shield. In particular, the inner protection cover is preferably attachable directly on the inner side of the eye protection shield. For example, the welding protector may have a window in which the eye protection shield is arranged and which forms a recess on the eye facing side of the eye protection shield. The inner protection cover may be shaped and sized to form a snap or press-fit with walls of the welding protector that form the recess.

In one embodiment the inner protection cover provides first retention means. The first retention means allow the magnifying cover to be attached to the inner protection cover. In particular the first retention means allow the magnifying cover to be attached at one or more positions in a dimension parallel to the vertical axis (or in the vertical dimension) relative to the inner protection cover. Thus, the magnifying cover may be positioned at different heights relative to the inner protection cover. The magnifying cover preferably has second retention means for engaging with the first retention means. The first retention means may comprise two flaps on opposite sides of the inner protection cover. Further, each flap may have a series of receptacles distributed along a dimension parallel to the vertical axis (or along the vertical dimension). The second retention means may comprise at least two retainers. Each of the retainers is provided for engaging in one of the receptacles. The retainers preferably protrude from opposite sides of the magnifying cover in opposite directions. In preferred embodiments the magnifying cover has two, three, four or more retainers on each of the opposite sides. Thus, skewing of the magnifying cover, for example during use, is prevented.

In one embodiment the magnifying cover has a first portion outside the optical lenses and a second portion forming optical lenses. The first and second portion forming one monolithic inner protection cover which is removably attachable in a position adjacent the inner side of the eye protection shield. Although in this embodiment the inner protection cover has integrated lenses it may be still possible to combine a further magnifying cover with the inner protection cover of this embodiment. Accordingly features described for the inner protection cover without integrated lenses may be provided in this embodiment identically.

In one embodiment the magnifying cover may be attached or laminated on the eye facing inner side of the eye protection shield by an adhesive. The adhesive may be selected to provide permanent adhesion, for example may be based on a thermosetting and/or cross-linkable adhesive. Further, the adhesive may be selected to provide temporary adhesion, for example by a (preferably removable) pressure sensitive adhesive. One suitable adhesive may have properties like the adhesive provided on Post-It® Notes available from 3M Company. The adhesive may be provided at a circumferential area of the magnifying cover, in particular in an area outside the lenses. Preferably the adhesive is provided at only a margin of the magnifying cover. Further, a clear adhesive may be provided for fully laminating the magnifying cover and the eye facing side of the eye protection shield together. In one embodiment the magnifying cover is flexible, for example may be generally flat if not forced toward a curved shape, but is conformable to the shape of the eye facing side of the eye protection shield without breaking.

In a further embodiment the magnifying cover is rigid, in particular may have a natural shape that corresponds to the shape of the eye protection shield.

The eye protection shield preferably comprises an electrically switchable light shielding device. Such an electrically switchable light shielding device may comprise liquid crystals. The liquid crystals are arranged in direct contact between a first and second alignment layer, the first and second alignment layer are arranged on a first and a second transparent electrode layer, respectively, and the first and second transparent electrode layer are arranged on a first and a second transparent layer, respectively. The first and a second transparent layer are each provided with a light polarizer. The light polarizers permit a transmission of light having a particular polarization only. Accordingly, the liquid crystals guide light of the particular polarization received from one polarizer toward the opposite polarizer. Depending on the orientation of the liquid crystals the light may be blocked or transmitted by the other polarizer so that the light shielding device is in the dark-state or the light-transmission-state, respectively.

In a preferred embodiment the eye protection shield comprises two light shielding devices arranged in optical sequence. This means that a light beam impinging on perpendicular on the eye protection shield passes both light shielding devices at least in the light-transmission-state. In such an embodiment one polarizer may be arranged between the two light shielding devices and the so formed sandwich of the two light shielding devices may be arranged between further two polarizers. Accordingly, such an embodiment has three polarizers and two light shielding devices. This is advantageous to provide a maximized darkening effect in the dark-state and a sufficient light transmission state in the light-transmission-state.

The welding protector may have a sensor and a control circuit. The sensor, the control circuit and the light shielding device preferably cooperate such that light of a certain minimum intensity received by the sensor causes the light shielding device to shut. Further, the sensor, the control circuit and the light shielding device preferably cooperate such that light of an intensity below that minimum intensity causes the shielding device to open. Thus, the welding protector can be worn in position during welding and under normal light condition without additional manual operation.

In an embodiment the curve underlying the curved eye protector, in particular the eye protection shield, is circular. The radius of the circle underlying the eye facing side of the eye protection shield may be between 80 mm and 90 mm, preferably 85 mm. Further, the side of the magnifying cover facing the eye facing side of the eye protection shield preferably has a shape and radius that corresponds to the shape and radius of the eye facing side of the eye protection shield. In particular, the side of the magnifying cover facing the eye facing side of the eye protection shield may be between 80 mm and 90 mm, preferably 85 mm.

The eye facing side of each lens of the magnifying cover may have a circular shape too. The eye facing side of each lens of the magnifying cover may, for example, be based on a cylindrical, spherical or a toric shape. The cylinder, sphere or torus may be based on a radius of between 110 mm and 120 mm, for example 116.9 mm. It is noted that the radius of the eye facing side of each lens will be typically selected in accordance to the desired diopters of the respective lens. Accordingly, the invention covers different radii of the eye facing side of the lenses.

In one embodiment at least one or both of the lenses comprise a Fresnel lens or are formed of a Fresnel lens.

In a further embodiment the optical lenses provide for a refractive power of between 1.0 and 3.0 Diopters. In particular, the optical lenses may be selected from a refractive power of 0.5, 1.0, 1.5, 2.0, 2.5 and 3.0 Diopters.

In a further embodiment the optical lenses are customized to a particular wearer. For example a wearer who also wears glasses normally may use an individual magnifying cover.

In a further aspect the invention relates to a kit of parts. The kit comprises a welding protector according to the invention and a plurality of magnifying covers. The kit may comprise at least two magnifying covers. The magnifying covers may have different magnifications selected from among 1.0, 1.5, 2.0, 2.5 and 3.0 Diopters.

BRIEF DESCRIPTION OF THE FIGURES

FIG. 2 is a perspective view of an inner protection cover according to an embodiment of the invention;

DETAILED DESCRIPTION OF THE INVENTION

Figure 1:
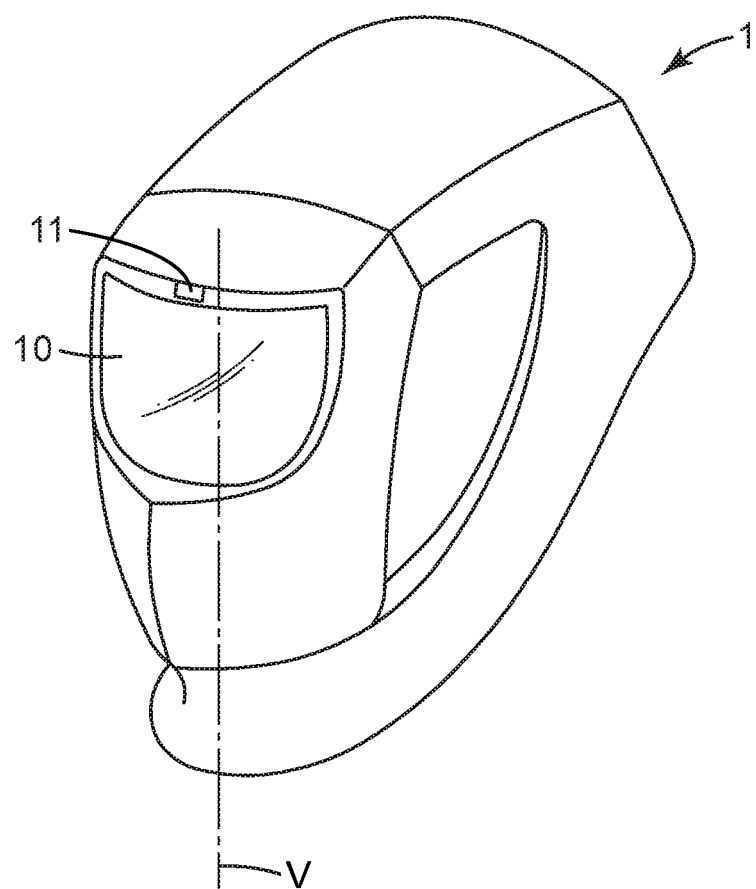
FIG. 1 is a perspective view of a welding protector according to an embodiment of the invention.

FIG. 1 shows a welding protector according to the invention in the form of a welding helmet 1. It is noted that although the example refers to a helmet the invention may be likewise used in combination with a welding shield which mainly covers the face of a wearers head. For the purpose of reference a vertical axis V is indicated in the example. The vertical axis V of the welding protector would be normally oriented in a dimension of the force gravity when worn by a wearer.

The welding helmet 1 comprises an eye protection shield 10. The eye protection shield 10 electrically switchable light filter for switching between a light-transmission-state and a dark-state. Such welding filters are sometimes referred to as Automatic Darkening Filters in the art of welding protection. In particular, the eye protection shield 10 is operable such that it switches from the light-transmission-state into the dark-state in response to light incident on a sensor 11. When switched in the dark-state, the eye protection shield 10 darkens so that light is hindered in being transmitted through eye protection shield 10 at its full intensity. This enables a user to observe a welding arc by seeing through the eye protection shield 10 without risking to be exposed to harmful light radiation from the welding arc. In the light-transmission-state the eye protection shield 10 allows the user to see under ambient light conditions (in the absence of the welding arc). The electrically switchable light filter in the example is based on a liquid crystal cell that comprises a liquid crystal layer located between two transparent substrates. In particular, each substrate has an electrode layer and an alignment layer. The electrode layer is a full-faced electrically conductive layer made of Indium Tin Oxide (ITO). The alignment layer may be made of polyimide that has been treated mechanically, such as by brushing or rubbing, in specific alignment directions. In particular, the liquid crystals are arranged in direct contact between a first and a second alignment layer. The first and second alignment layer are arranged on a first and a second transparent electrode layer, respectively, and the first and second transparent electrode layer are arranged on a first and a second transparent layer, respectively. The first and a second transparent layer preferably are each provided with a light polarizer. The first and second alignment layers are configured such that the liquid crystals are oriented so that the liquid crystal cell is in the light-transmission-state by default. A voltage applied to the electrode first and second layers causes the liquid crystal to re-orient so that the liquid crystal cell is in the dark-state.

The eye protection shield 10 in the example further has a band pass filter for attenuating the infra-red (IR) and ultraviolet (UV) wavelength components from high-intensity incident light. The band pass filter can be an interference filter that reflects the IR radiation and absorbs the UV-A, -B and -C components of the incident light.

The skilled person is aware of variations of Automatic Darkening Filters so that the scope of the invention is not limited to the particular welding filter described in this example.

Figure 3:
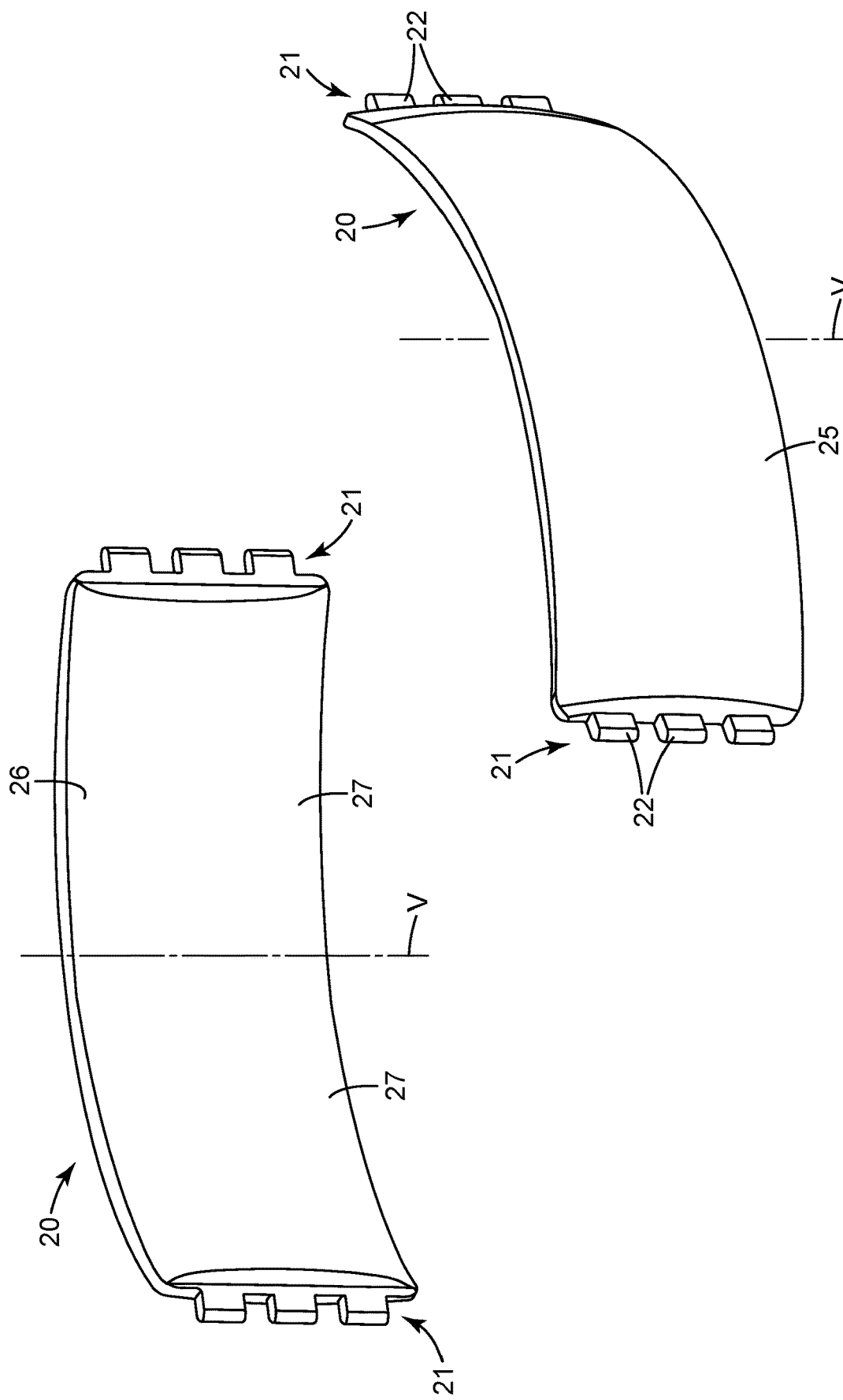
FIG. 3 is a perspective view of a magnifying cover according to an embodiment of the invention.
Figure 4:
FIG. 4 is a top view of an inner protection cover having an integrated magnifying cover according to an embodiment of the invention.
Figure 5:
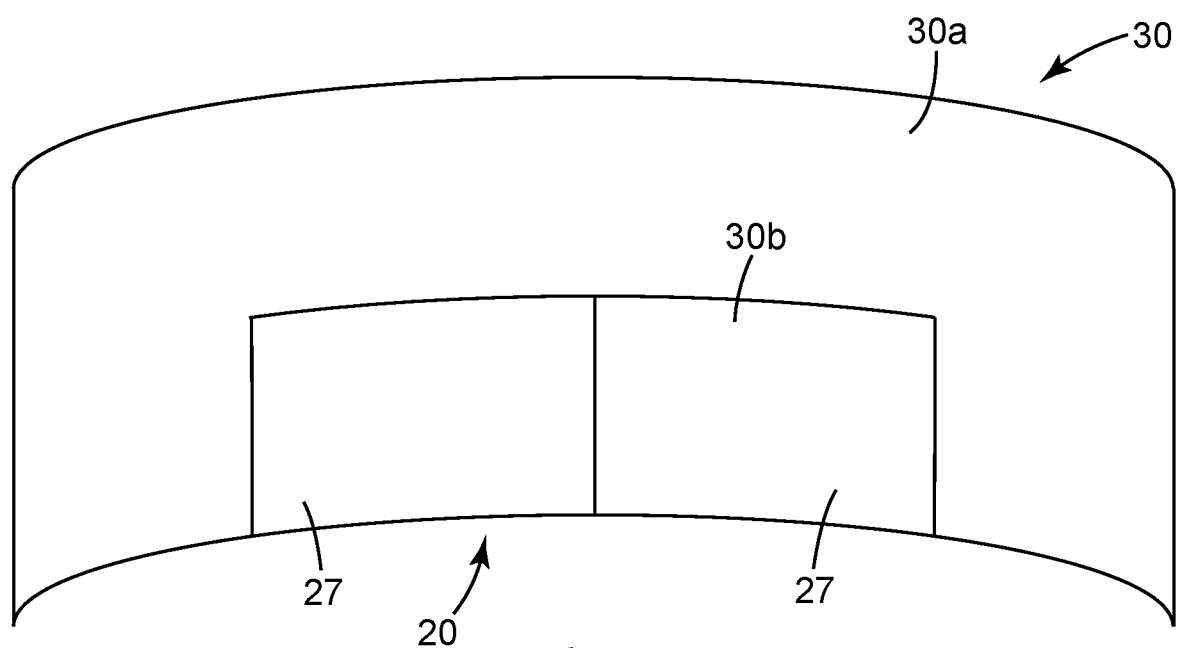
FIG. 5 is a rear view of the inner protection cover shown in FIG. 4.

The eye protection shield 10 has a magnifying cover 20 as shown in FIGS. 3, 4 and 5. The magnifying cover 20 may be integrated in an inner protection cover 30 as illustrated in FIGS. 4 and 5. Alternatively, the magnifying cover 20 may be separate from an inner protection cover 30 as shown in FIGS. 2 and 3. Further, a separate magnifying cover 20 (as shown in FIG. 3) may be combined with an inner protection cover 30 as shown in FIGS. 4 and 5.

Generally, although not illustrated, the inner protection cover 30, for example as shown in any of the FIG. 2, 3, 4 or 5 is attachable to an inner side of the eye protection shield. The inner side of the eye protection shield for the purpose of the present invention is the side which faces the wearer's eyes when the welding protector is worn. There exist a variety of possibilities for attaching the inner protection cover 30 to the eye protection shield. In the present example the eye protection shield is provided in a window of the helmet. The welding helmet in this window forms a recess behind (in a direction toward a wearer's eyes) the eye protection shield. The inner protection cover 30 and the recess are shaped and sized so that the inner protection cover 30 can be plugged or snapped into the recess for attachment to the eye protection shield. The snap connection is configured such that the inner protection cover 30 is removable. The inner protection cover protects the eye protection shield against scratches, dust and eventually glowing metal from welding and thus advantageously is replaceable. Accordingly, the inner protection cover 30 is replaceable by another inner protection cover if necessary.

FIG. 2 shows an inner protection cover 30 without integrated magnifying cover. However, the inner protection cover 30 has first retention means 31 at which a magnifying cover 20 (FIG. 3) can be retained. The magnifying cover 20 therefore has second retention means 21. In particular, the inner protection cover 30 has a pair of flaps 32 which each comprise a series of receptacles in the form of through-holes 33. The receptacles or through-holes 33 are uniformly distributed along a dimension parallel to a vertical axis V. The magnifying cover 20 has a series of pins or prongs 22 which are sized and distributed so that they can be mated with the through-holes 33. As shown the magnifying cover 20 has a height in a dimension of the vertical axis V which is smaller than the height of the inner protection cover 30 in the same dimension.

Accordingly, the magnifying cover 20 can be attached to multiple different positions along a dimension parallel to the vertical axis V. Therefore, with respect to any desire of magnifying an object during welding the wearer can adapt the welding protector as needed.

For attaching the magnifying cover 20 to the inner protection cover 30 the flaps 31 can be grasped to bend the inner protection cover 30 in a direction toward straightening the curved shape of the inner protection cover 30. Thereby the pair of flaps 31 move away from each other and provide the necessary space for the magnifying cover 20 to be inserted between the flaps 31 and to mate the prongs 22 with the through-holes 33.

The major portion of the inner protection cover 30 has a constant thickness and is preferably clear, colorless and transparent. Therefore the inner protection cover 30 does as such not provide for any significant optical effect. Further, the curve, which the curved shape of the inner protection cover 30 is based on preferably is based on a circular shape.

It has been found that therefore optical distortions with respect to a wearer viewing through the inner protection cover 30 can be minimized. The inner protection cover 30 of the example has a reinforced periphery. In particular, a circumferential bulge 34 is provided on the inner side 36 (the eye facing side) of the inner protection cover 30. Therefore, the inner protection cover 30 can be made relatively light weight and optically neutral and further is provided with a certain mechanical stiffness. The mechanical stiffness allows the inner protection cover 30 to by attached in the recess of the welding protect by spring force that is only provided by the inner protection cover 30. Additional retention means are therefore not necessary. Further, the mechanical stiffness enables the inner protection cover 30 also to safely retain the magnifying cover 20.

The inner protection cover 30 as well as the magnifying cover 20 are preferably molded from a plastic material. In particular, the plastic material may be selected from materials that are clear, colorless and transparent at least after molding. Suitable materials comprise polycarbonate (PC), polymethyl methacrylate (PMMA), polystyrene (PS), styrene acrylonitrile copolymer (SAN), or fluorinated polymers as available from 3M Company for example.

The inner side 36 forms one major side of the inner protection cover 30. Further, the inner protection cover 30 has a major outer side 35 opposite of the inner side 36. The outer side 35 is shaped to conform to the inner side of the eye protection shield. The inner side 36 (except for the bulge 34 in the margin) extends equidistant to the outer side 35. Further, the magnifying cover 20 has a major outer side 25 and a major inner side 26. The outer side 26 and the inner side 25 are shaped to, in combination, provide two optical lenses 27. The optical lenses 27 have a rectangular outline. Therefore, the area under which objects can be viewed through the optical lenses is maximized, in particular in the middle of the magnifying cover, where the optical lenses merge with one another. The outer side 26 of the magnifying cover 20 has a convex shape. In a horizontal plane that is perpendicular to the vertical axis V and that extends through the apex of the convex outer side 26 the outline of the outer side 26 at least essentially corresponds in shape to the curvature of the inner side 36 of the inner protection cover 30. Thus, the magnifying cover 20 and the inner protection cover 30 can be combined to form a relative compact assembly.

The inner protection cover 30 as shown in FIG. 5 combines the optical lenses 27 within the protection cover 30. The inner protection cover 30 in this example has a first portion 30a outside optical lenses 27 and a second portion 30b forming the optical lenses 27. The first and second portion 30a, 30b form one monolithic piece. Accordingly, a separate inner protection cover is optional. The lenses 27 except for the fact that they are monolithically integrated rather than being mounted are otherwise identical to the lenses described in FIG. 3. The attachment of the inner protection cover 30 at the welding protector may be identical with the embodiment shown in FIG. 2. In particular, the inner protection cover 30 may be snap fit in a recess of a window in which the eye protection shield is accommodated. Although not illustrated the inner protection cover 30 may also have flaps with optional through-holes. These flaps may in all embodiments also be used for bending the inner protection cover 30 towards a greater curvature during an operation of attaching the inner protection cover 30 to the welding protector. Further, also the materials as mentioned for the embodiments in FIGS. 2 and 3 may be likewise used for the embodiment shown in FIGS. 4 and 5.

The invention claimed is:

1. A welding protector comprising:
   an eye protection shield having an electrically switchable light filter, the eye protection shield having a curved shape about a vertical axis;
   an inner protection cover which is removably attachable in a position adjacent to an inner side of the eye protection shield; and
   a magnifying cover attachable to an eye facing inner side of the inner protection cover, wherein the magnifying cover is pre-shaped based on a curve that extends equidistant to the curve the eye protection shield is based on, and wherein the magnifying cover comprises two optical lenses which in combination only partially cover the eye protection shield.

2. The welding protector of claim 1, wherein the optical lenses have a rectangular outline and are arranged directly adjacent each other.

3. The welding protector of claim 1, wherein the inner protection cover provides first retention means allowing the magnifying cover to be attached at one or more positions in a dimension parallel to the vertical axis relative to the inner protection cover.

4. The welding protector of claim 3, wherein the magnifying cover has second retention means for engaging with the first retention means.

5. The welding protector of claim 4, wherein the first retention means comprises two flaps on opposite sides of the inner protection cover, with each flap having a series of receptacles distributed along a dimension parallel to the vertical axis, and wherein the second retention means comprises at least two retainers, each for engaging in one of the receptacles.

6. The welding protector of claim 1, wherein the magnifying cover has a first portion outside the optical lenses and a second portion forming optical lenses with the first and second portion forming one monolithic inner protection cover which is removably attachable in a position adjacent the inner side of the eye protection shield.

7. The welding protector of claim 1, wherein the eye protection shield comprises an electrically switchable light shielding device comprising liquid crystals arranged in direct contact between a first and second alignment layer, the first and second alignment layer being arranged on a first and a second transparent electrode layer, respectively, and the first and second transparent electrode layer are arranged on a first and a second transparent layer, respectively, and wherein the first and a second transparent layer are each provided with a light polarizer.

8. The welding protector of claim 7, further having a sensor and a control circuit, wherein the sensor, the control circuit and the light shielding device cooperate such that light of a certain minimum intensity received by the sensor causes the light shielding device to shut, and light of an intensity below that minimum intensity causes the shielding device to open.

9. The welding protector of claim 1, wherein the curve underlying the curved eye protector is circular.

10. The welding protector of claim 1, wherein the optical lenses provide for a refractive power of between 1.0 and 3.0 Diopters.

11. A kit of parts comprising a welding protector according to claim 1 and a plurality of magnifying covers, comprising at least two magnifying covers having different refractive power selected from among 1.0, 1.5, 2.0, 2.5 and 3.0 Diopters.

12. The welding protector of claim 1, wherein an outer surface of the inner protection cover is configured to conform with the inner side of the eye protection shield.

13. A welding protector comprising:
- an eye protection shield having an electrically switchable light filter, the eye protection shield having a curved shape about a vertical axis; and
- an inner protection cover which is removably attachable in a position adjacent to the inner side of the eye protection shield, wherein the inner protection cover further includes a magnifying cover fully integrated therein, wherein the magnifying cover is pre-shaped based on a curve that conforms to the curvature of the inner protection cover, and wherein the magnifying cover comprises two optical lenses which in combination only partially cover the eye protection shield.

* * * * *